(12) United States Patent
Goronzy et al.

(10) Patent No.: US 6,818,406 B2
(45) Date of Patent: Nov. 16, 2004

(54) RHEUMATOID ARTHRITIS MARKERS

(75) Inventors: Jorg J. Goronzy, Rochester, MN (US); Cornelia M. Weyand, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 155 days.

(21) Appl. No.: 09/816,814

(22) Filed: Mar. 23, 2001

(65) Prior Publication Data

US 2003/0027136 A1 Feb. 6, 2003

(51) Int. Cl.$^7$ .......................... G01N 33/53; C07K 14/52
(52) U.S. Cl. ....................... 435/7.1; 530/300; 530/350; 530/351; 530/389.2
(58) Field of Search .......................... 435/7.1; 530/300, 530/350, 351, 389.2, 388.22, 388.23, 391.1; 424/43.1, 145.1; 707/10; 705/2

(56) References Cited

U.S. PATENT DOCUMENTS

| | | | | | |
|---|---|---|---|---|---|
| 6,018,713 | A | * | 1/2000 | Coli et al. | 705/2 |
| 6,075,124 | A | * | 6/2000 | Li et al. | 530/351 |
| 6,088,695 | A | * | 7/2000 | Kara | 707/10 |
| 6,420,346 | B1 | * | 7/2002 | Karin | 514/44 |
| 6,555,320 | B1 | * | 4/2003 | Goronzy et al. | 435/7.1 |

OTHER PUBLICATIONS

Ellingsen et al., "In vitro migration of mononuclear cells towards synovial fluid and plasma from rheumatoid arthritis patients correlates to RANTES synovial fluid levels and to clinical pain parameters," *Scand. J. Rheumatol.*, 2000, 29:216–221.

Huissoon et al., "Increased expression of CD23 in rheumatoid synovitis," *Scand. J. Rheumatol.*, 2000, 29:154–159.

Peichl et al., "Presence of NAP–1/IL–8 in Synovial Fluids Indicates a Possible Pathogenic Role in Rheumatoid Arthritis," *Scand. J. Immunol.*, 1991, 34:333–339.

Strehlau et al., "Quantitative detection of immune activation transcripts as a diagnostic tool in kidney transplantation," *Proc. Natl. Acad. Sci. USA*, 1997, 94:695–700.

GenBank Accession No. AF044197.
GenBank Accession No. J03565.
GenBank Accession No. L11015.
GenBank Accession No. U88320.

Arnett et al., "The American Rheumatism Association 1987 Revised Citeria for the Classification of Rheumatoid Arthritis," *Arthritis. Rheum.*, 1988, 31(3):315–324.

Burmester et al., "Mononuclear Phagocytes and Rheumatoid Synovitis," *Arthritis Rheum.*, 1997, 40(1):5–18.

Cruikshank et al., "Lymphokine Activation of T4+ T Lymphocytes and Monocytes," *J. Immunol.*, 1987, 138(11): 3817–3823.

Feldman et al., "Rheumatoid Arthritis," *Cell*, 1996, 85(3):307–310.

Firestein and Zvaifler, "How Important Are T Cells In Chronic Rheumatoid Synovitis," *Arthritis Rheum.*, 1990, 33(6):768–773.

Fox, "The Role of T Cells in the Immunopathogenesis of Rheumatoid Arthritis," *Arthritis Rheum.*, 1997, 40(4): 598–609.

Goronzy and Weyand, "T Cells in Rheumatoid Arthritis," *Rheum. Dis. Clin. North Am.*, 1995, 21(3):655–674.

Hale and Haynes, "Pathology of Rheumatoid Arthritis and Associated Disorders," *Arthritis and Allied Conditions—A Textbook of Rheumatology*, Koopman (ed.), Williams & Wilkins, Baltimore, 1997, 13$^{th}$ Edition, vol. 1, Ch. 52, pp. 993–1016.

Harris, *Rheumatoid Arthritis*, WB Saunders Co., Philadelphia, 1997, Sections I–VI, pp. 3–212.

Panayi et al., "The Importance of the T Cell in Initiating and Maintaining the Chronic Synovitis of Rheumatoid Arthritis," *Arthritis Rheum.*, 1992, 35(7):729–735.

Todd et al., "A Molecular Basis for MHC Class II—Associated Autoimmunity," *Science*, 1988, 240:1003–1009.

* cited by examiner

Primary Examiner—Gary Kunz
Assistant Examiner—Nirmal S. Basi
(74) Attorney, Agent, or Firm—Fish & Richardson P.C., P.A.

(57) ABSTRACT

The invention provides methods and materials for evaluating arthritis conditions. Specifically, the invention provides methods and materials for determining the severity of an arthritis condition in a mammal that involve determining whether or not a sample from that mammal contains an elevated level of a CD21L polypeptide, a lymphotoxin-β polypeptide, or a chemoattractant polypeptide. The invention also provides methods and materials for assisting medical or research professionals in determining the severity of an arthritis condition in a mammal. In addition, the invention provides methods and materials related to kits that can be used to determine the severity of an arthritis condition.

4 Claims, 2 Drawing Sheets

RHEUMATOID ARTHRITIS MARKERS

STATEMENT AS TO FEDERALLY SPONSORED RESEARCH

Funding for the work described herein was provided by the federal government, which may have certain rights in the invention.

BACKGROUND

1. Technical Field

The invention relates to methods and materials involved in determining the severity of a rheumatoid arthritis condition.

2. Background Information

Rheumatoid arthritis (RA) affects individuals in the prime of their life and is feared because of its potential to cause chronic pain and irreversible damage of tendons, ligaments, joints, and bones. The symmetrical involvement of small peripheral joints has an enormous impact on hand and foot functions and poses therapeutic challenges that cannot be easily overcome by joint replacement. Also, systemic manifestations of RA are not rare and can range from relatively minor problems, such as rheumatoid nodules, to life-threatening organ disease.

In addition, RA is a systemic inflammatory disease that primarily manifests itself as synovial inflammation of diarthrodial joints. The typical histopathological changes include dense infiltration of the synovial membrane by mononuclear cells, neoangiogenesis, and hypertrophy and hyperplasia of the synovial lining (Harris (ed); Rheumatoid Arthritis, Philadelphia, WB Saunders Co., pp.3–212 (1997); and Hale and Haynes: Pathology of rheumatoid arthritis and associated disorders. Arthritis and Allied Conditions. A textbook of Rheumatology. Edited by Koopman. Baltimore, Williams & Wilkins, pp.993–1016 (1997)). The etiopathogenesis of the syndrome is not well understood. Several lines of evidence support a central role of T lymphocytes in the disease-specific pathogenic events (Todd et al., *Science*, 240:1003–1009 (1988); Panayi et al., *Arthritis Rheum.*, 35:729–735 (1992); and Goronzy and Weyand, *Rheum. Dis. Clin. North Am.*, 21:655–674 (1995)). An alternative hypothesis, namely, that macrophages are the pivotal cell type in rheumatoid synovitis, has also been proposed (Firestein and Zvaifler, *Arthritis Rheum.* 33:768–773 (1990); and Burmester et al., *Arthritis Rheum.*, 40:5–18 (1997)). Whether only T cells or only macrophages or both are the causative elements in RA remains a matter of controversy (Feldmann et al., *Cell*, 85:307–310 (1996); and Fox, *Arthritis Rheum.*, 40:598–609 (1997)).

RA is primarily a clinical diagnosis. Symmetrical joint involvement, dominant manifestations in peripheral joints, rheumatoid factor production, and the formation of rheumatoid nodules are considered when the diagnosis is made (Arnett et al., *Arthritis Rheum.*, 31:315–324 (1988)). The histological appearance of the synovium varies quite extensively. In addition, no information is available on the mechanisms underlying the topographical arrangement of the inflammatory infiltrate in the rheumatoid synovium.

SUMMARY

The invention involves evaluating arthritis conditions. Specifically, the invention provides methods and materials related to determining the severity of an arthritis condition in a mammal. The term "arthritis condition" as used herein refers to an infective, autoimmune, or traumatic inflammatory condition that affects a joint. Arthritis conditions can be acute or chronic. A chronic arthritis condition is referred to as rheumatoid arthritis (RA).

RA conditions range from mild to severe. Typically, a patient with a mild rheumatoid arthritis condition experiences pain, swelling, heat, and loss of joint function to a lesser extent than a patient with a severe rheumatoid condition. In addition, patients with sever RA can have one or more germinal centers in an affected joint. A germinal center is a site where B cells proliferate, leading to an increased immune response.

The methods and materials described herein can be used to identify arthritis patients that have either a mild or severe arthritis condition. The ability to distinguish between mild and severe arthritis conditions can help alleviate pain in patients with arthritis by providing appropriate treatments in a timelier manner. In addition, the invention provides methods and materials that can be used to assist medical or research professionals in determining the severity of an arthritis condition. With this assistance, medical or research professionals can assess the treatment needs of arthritis patients with greater accuracy, improving the prognosis of the disease.

In general, the invention features a method for determining the severity of an arthritis condition in a patient. The method includes determining whether or not a sample from the mammal contains an elevated level of a CD21L polypeptide, where the presence of the elevated level indicates that the arthritis condition is severe. The arthritis condition can be rheumatoid arthritis. The sample can be a tissue sample (e.g., a synovial tissue sample). The presence or absence of the elevated level can be determined by measuring a CD21L polypeptide or a CD21L mRNA.

In another embodiment, the invention features a method for determining the severity of an arthritis condition in a mammal. The method includes determining whether or not a sample from the mammal contains an elevated level of a lymphotoxin-$\beta$ polypeptide, where the elevated level indicates that the arthritis condition is severe.

Another embodiment of the invention features a method for determining the severity of an arthritis condition in a patient. The method includes determining whether or not a sample from the mammal contains an elevated level of a chemoattractant polypeptide, where the elevated level indicates that the arthritis condition is severe. The chemoattractant can be a B-lymphocyte chemoattractant polypeptide.

Another embodiment of the invention features a method for determining the severity of an arthritis condition in a mammal. The method includes determining whether or not a sample from the mammal contains at least one marker, the marker being an elevated level of a CD21L polypeptide, an elevated level of a lymphotoxin-$\beta$ polypeptide, or an elevated level of a chemoattractant polypeptide, where the presence of the at least one marker indicates that the arthritis condition is severe. The arthritis condition can be rheumatoid arthritis. The mammal can be a human. The sample can be a tissue sample (e.g., a synovial tissue sample). The at least one marker can be the elevated level of a CD21L polypeptide. The at least one marker can be the elevated level of a lymphotoxin-$\beta$ polypeptide. The at least one marker can be the elevated level of a chemoattractant polypeptide. The chemoattractant can be a B-lymphocyte chemoattractant polypeptide. The method can include determining whether or not the sample contains at least two of the markers. The method can include determining whether or not the sample contains at least three of the markers. The method can include determining whether or not the sample contains at least four of the markers.

In another embodiment the invention features a method of assisting a person in determining the severity of an arthritis condition in a patient. The method includes (a) determining whether or not a sample from the patient contains an elevated level of a CD21L polypeptide, and (b) communicating information about the presence or absence of the elevated level in the sample to the person, where the presence of the elevated level indicates that the arthritis condition is severe. The person can be a medical or research professional. The person can be a doctor, a nurse practitioner, a research scientist, or a research technician. The arthritis condition can be rheumatoid arthritis. The sample can be a tissue sample (e.g., a synovial tissue sample). The communication can include sending the information directly to the person. The communication can include sending the information indirectly to the person. The communication can include making the information electronically available to the person.

Another embodiment of the invention features a method of assisting a person in determining the severity of an arthritis condition in a patient. The method includes (a) determining whether or not a sample from the patient contains an elevated level of a lymphotoxin-β polypeptide, and (b) communicating information about the presence or absence of the elevated level in the sample to the person, where the presence of the elevated level indicates that the arthritis condition is severe.

Another embodiment of the invention features a method of assisting a person in determining the severity of an arthritis condition in a patient. The method includes (a) determining whether or not a sample from the patient contains an elevated level of a chemoattractant polypeptide, and (b) communicating information about the presence or absence of the elevated level in the sample to the person, where the presence of the elevated level indicates that the arthritis condition is severe. The chemoattractant polypeptide can be a B-lymphocyte chemoattractant polypeptide.

Another embodiment of the invention features a method of assisting a person in determining the severity of an arthritis condition in a mammal. The method includes (a) determining whether or not a sample from the mammal contains at least one marker, the marker being an elevated level of a CD21L polypeptide, an elevated level of a lymphotoxin-β polypeptide, or an elevated level of a chemoattractant polypeptide, and (b) communicating information about the presence or absence of the at least one marker in the sample to the person, where the presence of the at least one marker indicates that the arthritis condition is severe. The person can be a medical or research professional. The person can be a doctor, a nurse practitioner, a research scientist, or a research technician. The arthritis condition can be rheumatoid arthritis. The mammal can be a human or rodent. The sample can be a tissue sample (e.g., a synovial tissue sample). The at least one marker can be the elevated level of a CD21L polypeptide. The at least one marker can be the elevated level of a lymphotoxin-β polypeptide. The at least one marker can be the elevated level of a chemoattractant polypeptide. The chemoattractant polypeptide can be a B-lymphocyte chemoattractant polypeptide. The communication can include sending the information directly to the person. The communication can include sending the information indirectly to the person. The communication can include making the information electronically available to the person. The method can include determining whether or not the sample contains at least two of the markers. The method can include communicating information about the presence or absence of the at least two markers in the sample to the person. The method can include determining whether or not the sample contains at least three of the markers. The method can include communicating information about the presence or absence of the at least three markers in the sample to the person. The method can include determining whether or not the sample contains at least four of the markers. The method can include communicating information about the presence or absence of the at least four markers in the sample to the person.

In another aspect, the invention features a kit containing at least two oligonucleotide primer pairs, where each of the primer pairs amplifies a different target nucleic acid sequence, where the target nucleic acid sequence is a CD21L nucleic acid, a lymphotoxin-β nucleic acid, or a B-lymphocyte chemoattractant nucleic acid.

In another embodiment, the invention features an article of manufacture containing at least two oligonucleotide primer pairs and a label or package insert indicating that each of the at least two oligonucleotide primer pairs can amplify a different target sequence in an amplification reaction, where each target sequence is a CD21L nucleic acid, a lymphotoxin-β nucleic acid, or a B-lymphocyte chemoattractant nucleic acid.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
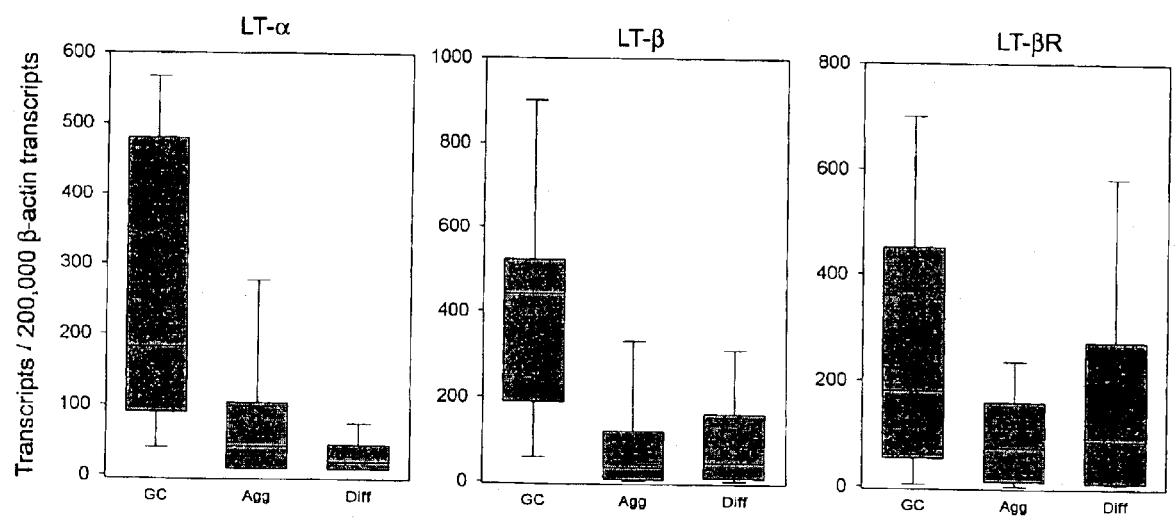
FIG. 1 is a bar graph plotting the ratio of LT-α, LT-β, or LT-β receptor transcripts to 200,000 β-actin transcripts versus lymphoid microstructure. The line within the box represents the medians, the box represents the $25^{th}$ and $75^{th}$ percentiles, and the whiskers represent the $10^{th}$ and $90^{th}$ percentiles.

The invention provides methods and materials related to evaluating arthritis conditions. Specifically, the invention provides methods and materials related to determining the severity of an arthritis condition in a mammal (e.g., human, dog, cat, horse, cow, goat, pig, and rodent). For example, the invention provides methods and materials for determining whether or not a sample from a mammal contains an elevated level of a CD21L polypeptide, a lymphotoxin-β polypeptide, or a chemoattractant polypeptide. As disclosed herein, if the level of a CD21L polypeptide, a lymphotoxin-β polypeptide, or a chemoattractant polypeptide in a sample is an elevated level, then the arthritis condition can be classified as severe. If the level of a CD21L polypeptide, a lymphotoxin-β polypeptide, or a chemoattractant polypeptide in a sample is not an elevated level, then the arthritis condition can be classified as not severe.

The level of a CD21 L polypeptide can be determined by measuring any CD21 L polypeptide including, without limitation, native and mutant CD21L polypeptides. Examples of CD21L polypeptides include, without limitation, human CD21L polypeptides (e.g., GenBank® accession number J03565), equine CD21L, canine CD21L, and mouse CD21L. The level of a lymphotoxin-β polypeptide can be determined by measuring any lymphotoxin-β polypeptide including, without limitation, native and mutant lymphotoxin-β polypeptides. Examples of lymphotoxin-βpolypeptides include, without limitation, human lymphotoxin-β (e.g., GenBank® accession number L11015) equine lymphotoxin-β, canine lymphotoxin-β, and mouse lymphotoxin-β. The term "chemoattractant polypeptide" as used herein refers to a polypeptide that directs the migration of a cell in the chemotaxis assay described by Cruikshank et al. (Cruikshank et al., *J. Immunol.* 138:3817–3825 (1987)). Examples of chemoattractant polypeptides include, without limitation, B-lymphocyte chemoattractant polypeptides (e.g., GenBank® accession number AF044197) and secondary lymphoid tissue cytokines (e.g., GenBank® accession number U88320).

The term "elevated level" as used herein with respect to the level of a CD21L polypeptide, a lymphotoxin-β polypeptide, or a chemoattractant polypeptide is any level that is greater than a reference level for a CD21L polypeptide, a lymphotoxin-polypeptide, or a chemoattractant polypeptide. The term "reference level" as used herein with respect to a CD21 L polypeptide, a lymphotoxin-β polypeptide, or a chemoattractant polypeptide is the level of a CD21L polypeptide, a lymphotoxin-β polypeptide, or a chemoattractant polypeptide typically expressed by mammals having mild RA. For example, a reference level of CD21L polypeptide can be the average level of CD21L polypeptide that is present in samples obtained from a random sampling of 50 patients with mild RA. Again, mammals with a mild RA condition experience pain, swelling, heat, and loss of joint function to a lesser extent than mammals with a severe RA condition. Typically, a mammal with a mild RA condition has joint tissue lacking germinal centers.

It will be appreciated that levels from comparable samples are used when determining whether or not a particular level is an elevated level. For example, the average level of lymphotoxin-β polypeptide present in synovial tissue from a random sampling of RA patients may be 30 units/g of synovial tissue, while the average level of lymphotoxin-β polypeptide present in blood tissue from the same random sampling of RA patients may be 10 units/g of blood tissue. In this case, the reference level for lymphotoxin-β polypeptide in synovial tissue would be 30 units/g of synovial tissue, and the reference level for lymphotoxin-β polypeptide in blood tissue would be 10 units/g of blood tissue. Thus, when determining whether or not the level of lymphotoxin-β polypeptide measured in synovial tissue is elevated, the measured level would be compared to the reference level for lymphotoxin-β polypeptide in synovial tissue (i.e., 30 units/g of synovial tissue).

An elevated level of a CD21L polypeptide, a lymphotoxin-β polypeptide, or a chemoattractant polypeptide can be any level provided that the level is greater than a corresponding reference level for a CD21L polypeptide, a lymphotoxin-β polypeptide, or a chemoattractant polypeptide. For example, an elevated level of B-lymphocyte chemoattractant polypeptide can be 0.5, 1, 2, 3, 4, 5, 6, 7, 8, 9, 10, 15, 20, or more times greater than the reference level for B-lymphocyte chemoattractant. In addition, a reference level can be any amount. For example, a reference level for CD21L polypeptide can be zero. In this case, any level of CD21L polypeptide greater than zero would be an elevated level.

Any method can be used to determine the level of a CD21L polypeptide, a lymphotoxin-β polypeptide, or a chemoattractant polypeptide present within a sample. For example, fluorescent activated cell sorting (FACS) analysis can be used to determine the level of a CD21L polypeptide present within a sample. Briefly, a cell sample can be obtained and stained with anti-CD21L antibodies such that the number of cells expressing CD21L is determined. In this case, the level of a CD21L polypeptide present within a sample is determined by evaluating the number of cells expressing CD21L polypeptide. In other words, comparing the number of CD21L polypeptide-expressing cells (e.g., percent of cells positive) within samples can be used to determine whether or not a particular sample contains an elevated level of a CD21L polypeptide. Alternatively, the level of a CD21L polypeptide, a lymphotoxin-β polypeptide, or a chemoattractant polypeptide present within a sample can be determined using other polypeptide detection methods such as western blot and immunochemistry techniques. Another method that can be used to determine the level of a CD21L polypeptide, a lymphotoxin-β polypeptide, or a chemoattractant polypeptide present within a sample can be functional. For example, a chemotaxis assay can be used to determine whether or not a synovial fluid sample contains an elevated level of a chemoattractant polypeptide.

The level of a CD21L polypeptide, a lymphotoxin-β polypeptide, or a chemoattractant polypeptide present within a sample also can be determined by measuring the level of an mRNA that corresponds to a CD21L polypeptide, a lymphotoxin-β polypeptide, or a chemoattractant polypeptide. Any method can be used to measure the level of a CD21L mRNA, a lymphotoxin-β mRNA, or a chemoattractant mRNA including, without limitation, PCR-based methods. For example, RT-PCR can be used with oligonucleotide primers designed to amplify CD21L mRNA. Any method can be used to identify primers capable of amplifying a CD21L mRNA, a lymphotoxin-β mRNA, or a chemoattractant mRNA. For example, a computer algorithm can be used to search a database (e.g., GenBank®) for CD21L, lymphotoxin-β, or a chemoattractant nucleic acid or amino acid sequences. Examples of oligonucleotide primer sequences for amplifying a CD21L mRNA include 5'-GTGGATTTACTTTGAAGGGCA-3' (SEQ ID NO: 1) and 5'-GGCATGTTTCTTCACACC-3' (SEQ ID NO: 2). Examples of oligonucleotide primer sequences for amplifying a lymphotoxin-β mRNA include 5'-ATCAGGGAGGACTGGTAACGGA-3' (SEQ ID NO: 3) and 5'-GAGGTAATAGAGGCCGTCCTGC-3' (SEQ ID NO: 4). Examples of oligonucleotide primer sequences for amplifying a B-lymphocyte chemoattractant mRNA include 5'-TCTCTGCTTCTCATGCTGCTGG-3' (SEQ ID NO: 5) and 5'-AGCTTGAGGGTCCACACACACA-3' (SEQ ID NO: 6). Any method can be used to analyze the amplified products. For example, amplified products corresponding to a CD21L mRNA can be separated by gel electrophoresis, and the level of CD21L-specific product determined by densiotometry. Alternatively, the level of CD21L-specific product can be determined by an ELISA technique.

Any type of sample can be used to evaluate the level of a CD21L polypeptide, a lymphotoxin-β polypeptide, or a chemoattractant polypeptide including, without limitation, synovial tissue or synovial fluid. In addition, any method can be used to obtain a sample. For example, a synovial tissue sample can be obtained by joint biopsy. Once obtained, a sample can be manipulated prior to measuring the level of a CD21L polypeptide, a lymphotoxin-β polypeptide, or a chemoattractant polypeptide. For example, a synovial tissue sample can be treated such that total mRNA is obtained. Once obtained, the total mRNA can be evaluated to determine the level of CD21L mRNA, chemoattractant mRNA, or lymphotoxin-β mRNA present. In another example, a synovial tissue sample can be disrupted to obtain a population of individual cells. Once obtained, the cells can be prepared for FACS analysis to determine the level of CD21L polypeptide present within the sample.

The invention provides for kits that can be used to determine whether or not a sample contains an increased level of a CD21L polypeptide, a lymphotoxin-β polypeptide, or a chemoattractant polypeptide by measuring the level of a CD21L mRNA, a lymphotoxin-β mRNA, or a chemoattractant mRNA. Such kits can contain at least two pairs of oligonucleotide primers. Each of the oligonucleotide primer pair can be used to amplify a different target sequence during a PCR. For example, one target sequence can be a B-lymphocyte chemoattractant mRNA while another target sequence is a lymphotoxin-β mRNA. The kits provided herein also can contain (1) a reference chart that indicates a reference level for a particular polypeptide or mRNA, (2) a positive control sample, and/or (3) a negative control sample. The positive control sample can be a sample that contains a known amount of a CD21L nucleic acid, a lymphotoxin-β nucleic acid, or a chemoattractant nucleic acid, while the negative control sample can be a sample that lacks CD21L nucleic acid, lymphotoxin-β nucleic acid, or chemoattractant nucleic acid. The kits can be configured in any type of design (e.g., microtiter plate design) and can be made of any type of material (e.g., plastic).

The invention also provides methods and materials to assist medical or research professionals in determining the severity of an arthritis condition in a mammal. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the level of a CD21L polypeptide, a lymphotoxin-β polypeptide, or a chemoattractant polypeptide in a sample, and (2) communicating information about one or more of those levels to that professional.

Any method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

The invention will be further described in the following examples, which do not limit the scope of the invention described in the claims.

EXAMPLES

Example 1

Synovial Lymphoid Microstructures

Synovial tissue samples were obtained at the time of joint surgery from 64 patients with active rheumatoid arthritis (RA). The samples were frozen, embedded in OCT (Sakura Finetek USA, Torrance, Calif.), and cut into 5 µm sections. The sections were mounted on slides (SuperFrost/Plus, Fisher Scientific, Pittsburgh, Pa.) and stored at −70° C. Before staining, the sections were fixed in acetone for 10 minutes, air dried, and further fixed in 1% paraformaldehyde/EDTA (pH=7.2) for 3 minutes. Endogenous peroxidase activity in the sections was blocked with 0.3% $H_2O_2$ in 0.1% sodium azide. Non-specific binding was blocked with 5% porcine serum for 15 minutes. The blocked sections were incubated with mouse anti-human LT-α1/β2 mAb (1:200) for 30 minutes at room temperature. After a thorough washing, the labeled sections were treated for 30 minutes with the EnVision+ reaction reagent (DAKOUSA, Carpinteria, Calif.) and developed with 3,3'-diaminobenzidine tetrahydrochloride (DAB). The DAB-stained sections were washed with tap water and subsequently blocked for 15 minutes with 5% goat serum. After this 15 minute blocking step, the sections were stained with mouse anti-human CD20 mAb (1:100; DAKOUSA) for 60 minutes at room temperature. After incubation with biotinylated rabbit anti-mouse Ig antibody (1:300; DAKOUSA), the labeled sections were incubated with VectaStain ABC-AP (Vector Laboratories, Burlingame, Calif.) for 30 minutes and then developed with Vector Red substrate (Vector Laboratories) for 3 minutes. The negative controls were sections incubated with the secondary antibody and not the primary antibodies. Once developed, the sections were counterstained with hematoxylin for 5 seconds and mounted in Cytoseal-60 (Stephens Scientific, Riverdale, N.J.). A pathologist analyzed the resulting double-labeled hematoxylin sections to determine the arrangement of T cells, B cells, macrophages, and dendritic cells within each sample. Each sample was subsequently grouped into one of three categories. The first category contained samples with a diffuse infiltration of T cells and B cells (no lymphoid organization). The second category contained samples with B cell-T cell follicles lacking germinal centers ($GC^-$ follicles). The third category contained samples with GC-positive B cell-T cell follicles ($GC^+$ follicles).

Thirty-six of the 64 samples analyzed were found to have cells diffusely arranged. Thirteen of the 64 samples analyzed were found to have cells organized into $GC^-$ follicles. Fifteen of the 64 samples analyzed were found to have cells organized into $GC^+$ follicles. Thus, 56.3% of the samples analyzed were placed in the first category, 20.3% of the samples analyzed were placed in the second category, and 23.4% of the samples analyzed were placed in the third category. These results demonstrate that a tissue sample from an RA patient can be placed into one of three different categories based on lymphoid organization.

Example 2

CD21L Identifies Rheumatoid Arthritis Samples with $GC^+$ Follicles

A portion of each of the synovial tissue samples described in Example 1 was used to isolate RNA. Total RNA was extracted from each portion using TRIzol® (Life Technologies). Once extracted, the total RNA was used in an RT-PCR with primers designed to amplify CD21L sequences. The sequences of the CD21L primers were 5'-GTGGATTTACTTTGAAGGGCA-3' (SEQ ID NO: 1) and 5'-GGCATGTTTCTTCACACC-3' (SEQ ID NO: 2). Primers designed to amplify β-actin were used as a control. The sequences of the β-actin primers were 5'-ATGGCCACGGCTGCTTCCAGC-3' (SEQ ID NO: 7) and 5'-CATGGTGGTGCCGCCAGACAG-3' (SEQ ID NO: 8). Following the RT-PCR, the amplified products were separated by 2% agarose gel electrophoresis.

Amplified products corresponding to CD21L were detected in 15 of the 64 samples (23.4%). All of these 15 samples positive for CD21L were from samples found to have cells organized into GC⁺ follicles when analyzed in Example 1. No CD21L signal was detected in the remaining 49 of 64 samples.

These results demonstrate that the presence of CD21L in a sample can predict the presence of GC⁺ follicles. These results also demonstrate that CD21L can be used as a marker to determine the severity of an RA condition. In summary, detecting CD21L in a sample can indicate that that sample came from a patient with a severe RA condition.

Example 3

Tissue Cytokine and Chemokine Levels Correlate to Lymphoid Cell Organization in a Sample Total RNA described in Example 2 was used in an RT-PCR with primers designed to amplify β-actin. The sequences of the β-actin primers were 5'-ATGGCCACGGCTGCTTCCAGC-3' (SEQ ID NO: 7) and 5'-CATGGTGGTGCCGCCAGACAG-3' (SEQ ID NO: 8). The resulting RT-PCR amplification products were analyzed for β-actin transcripts by semiquantitative PCR-ELISA. Following β-actin transcript analysis, each sample containing RT-PCR amplification products was adjusted to contain an equal amount of β-actin transcripts. Once adjusted, the samples were amplified by PCR with primers for lymphotoxin α (LT-α), lymphotoxin β (LT-β), B-lymphocyte chemoattractant (BLC), secondary lymphoid tissue cytokine (SLC), dendritic cell-derived C-C chemokine (DC-CK 1), macrophage chemoattractant protein-1 (MCP-1), or β-actin. The sequences of the primers were as follows:

LT-α
5'- GCTGCTCACCTCATTGGAGA -3'    (SEQ ID NO:9)

5'- GGTGGATAGCTGGTCTCCCT -3'    (SEQ ID NO:10)

LT-β
5'- ATCAGGGAGGACTGGTAACGGA -3'  (SEQ ID NO:3)

5'- GAGGTAATAGAGGCCGTCCTGC -3'  (SEQ ID NO:4)

BLC
5'- TCTCTGCTTCTCATGCTGCTGG -3'  (SEQ ID NO:5)

5'- AGCTTGAGGGTCCACACACACA -3'  (SEQ ID NO:6)

SLC
5'- CCCCAGGACCCAAGGCAGTGAT -3'  (SEQ ID NO:11)

5'- TGTGACCGCTCAGTCCTCTTGC -3'  (SEQ ID NO:12)

-continued

DC-CK 1
5'-GGTGTCATCCTCCTAACCAAG -3'    (SEQ ID NO:13)

5'-GGAAAGGGGAAAGGATGATA -3'     (SEQ ID NO:14)

MCP-1
5'- GCTCAGCCAGATGCAATCAA -3'    (SEQ ID NO:15)

5'- GCAATTTCCCCAAGTCTCTG -3'    (SEQ ID NO:16)

Each PCR amplification cycle consisted of a denaturing step at 94° C. for 30 seconds, an annealing step for 1 minute, and an elongating step at 72° C. for 1 minute. The annealing temperatures for the various primers were 55° C. for β-actin, BLC, LT-β, DC-CK 1, and MCP-1, 58° C. for LT-α, and 60° C. for SLC. Each reaction began with a single denaturing step at 94° C. for 10 minutes and ended with a single elongating step at 72° C. for 10 minutes. During the reactions, the amplification products were labeled with digoxygenin-11-dUTP (Roche Molecular Biochemicals—Boehringer Mannheim, Indianapolis, Ind.). Once labeled, the amplification products were semiquantified using an ELISA kit (PCR-ELISA, Roche Molecular Biochemicals—Boehringer Mannheim). Briefly, the ELISA kit protocol involved hybridizing the labeled amplification products to biotinylated internal probes specific for the sequences of interest. The sequences of the probes were as follows:

β-actin
5'- TTCCTTCCTGGGCATGGAGT -3' (SEQ ID NO:17)

LT-α
5'- CCAGTGGCATCTACTTCGTCTAC -3' (SEQ ID NO:18)

LT-β
5'- GAGGAGCCAGAAACAGATCTCAG -3' (SEQ ID NO:19)

BLC
5'- TCCCTAGACGCTTCATTGATCG -3' (SEQ ID NO:20)

SLC
5'- CTCCATCCCAGCTATCCTGTTC -3' (SEQ ID NO:21)

DC-CK 1
5'- CTTTTAAGAGTCCCATCTGCTATG -3' (SEQ ID NO:22)

MCP-1
5'- GAAGACTTGAACACTCACTCCAC -3' (SEQ ID NO:23)

To perform the hybridization, the labeled amplification products were incubated with 200 ng/mL probe at 42° C. for -actin, 50° C. for DC-CK 1 and MCP-1, and 55° C. for LT-α, LT-β, LT-βBR, BLC, and SLC. After 2.5 hours of incubation, the resulting hybrids were immobilized on streptavidin-coated microtiter plates. After washing, the hybrids were labeled with a peroxidase-conjugated anti-digoxigenin antibody. Peroxidase activity was detected using ABTS (2,2'-azino-di-[3-ethylbenzthiazoline sulfonate (6)] diammonium salt) substrate and quantified using a kinetic microplate reader (Molecular Devices, Sunnyvale, Calif.). The number of cytokine- or chemokine-specific transcripts was determined using a standard curve and expressed as the number of cytokine or chemokine transcripts per $1 \times 10^6$ β-actin transcripts.

Samples with GC⁺ follicles were found to contain higher levels of LT-α and LT-β transcripts when compared to the levels measured in either samples with GC⁻ follicles or samples with no lymphoid organization (FIG. 1). In samples with GC⁺ follicles, the median LT-α and LT-β transcript numbers were 182 and 441, respectively. In samples with GC⁻ follicles, the median LT-α and LT-β transcript numbers were 42 and 35, respectively. In samples with no lymphoid organization, the median LT-α and LT-β transcript numbers were 10 and 43, respectively.

Figure 2:
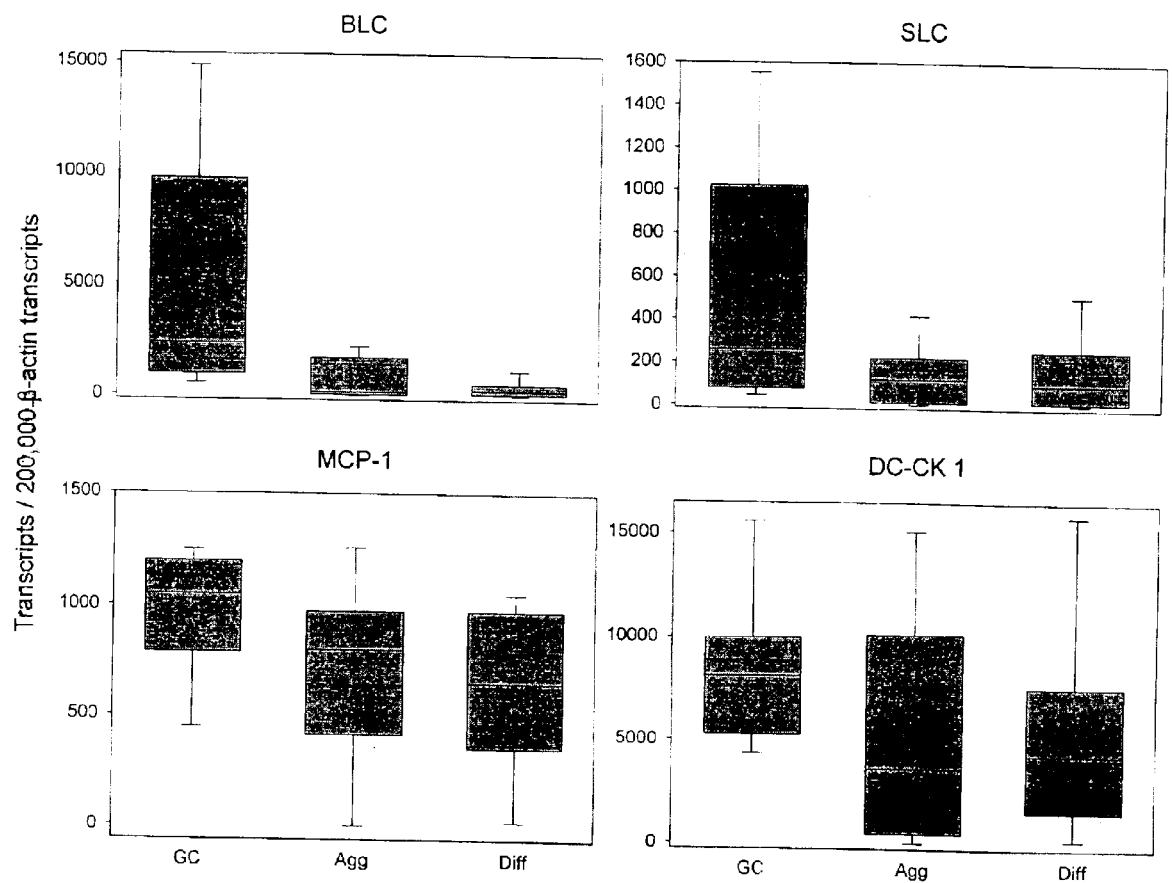
FIG. 2 is a bar graph plotting the ratio of BLC, SLC, MCP-1, or DC-CK 1 transcripts to 200,000 β-actin transcripts versus lymphoid microstructure. The line within the box represents the medians, the box represents the 25th and 75th percentiles, and the whiskers represent the 10th and 90th percentiles.

Samples with GC⁺ follicles were also found to contain higher levels of BLC and SLC transcripts when compared to the levels measured in either samples with GC⁻ follicles or samples with no lymphoid organization (FIG. 2). In samples with GC⁺ follicles the median BLC and SLC transcript numbers were 2139 and 212, respectively. In samples with GC⁻ follicles, the median BLC and SLC transcript numbers were 159 and 124, respectively. In samples with no lymphoid organization, the median BLC and SLC transcript numbers were 97 and 88, respectively.

To rule out the possibility that the elevated levels of BLC and SLC in samples with GC⁺ follicles were artifacts of increased inflammatory activity, two additional chemokines, DC-CK 1 and MCP-1, were analyzed. All samples contained transcripts for DC-CK 1 and MCP-1. Median DC-CK 1 and MCP-1 transcript numbers were not statistically different across all samples analyzed.

These results demonstrate that LT-α, LT-β, BLC, and SLC transcript levels are elevated in samples with GC⁺ follicles compared to the levels measured in either samples with GC⁻ follicles or samples with no lymphoid organization. In addition, these results indicate that the detection of an elevated level of a cytokine or chemokine such as LT-α, LT-β, BLC, or SLC in a sample can be used to predict the severity of an RA condition.

Example 4

Predicting the Presence of GC⁺ Follicles in a Sample by Logistic Regression Modeling of Cytokine/Chemokine Transcript Levels In situ cytokine/chemokine production was compared by nonparametric testing using SigmaStat software (SPPS, Chicago, Ill.). Cytokine and chemokine transcript levels were analyzed as continuous variables. Following this analysis the continuous variables were transformed into discrete variables by recursive partitioning to define optimal transcript level cutoffs. After identifying the cutoffs, logistic models were used to identify discrete variables that correlated with an increased likelihood of GC⁺ follicle presence in a sample. This analysis was done using SAS statistical software.

Although several continuous variables distinguished samples with and without GC⁺ follicles, none of these variables had a Gaussian distribution. Thus, each continuous variable was transformed into a discrete variable by recursive partitioning. Logistic regression analysis was performed to determine whether any discrete variables correlated with GC⁺ follicle presence. In the univariate analysis, high concentrations of LT-α, LT-β, BLC, SLC, DC-CK 1, and MCP-1 were predictive of GC⁺ follicles. LTβ BLC, transcript level were, however, the most powerful predictors of GC⁺ follicle presence in a sample. The probability of encountering GC⁺ follicles in a sample was 31-fold higher if LT-β-transcripts were present at levels above 315. Similarly, BLC transcript levels higher than 1,800 increased the probability of encountering GC⁺ follicles in a sample by a factor of 31.

Multivariate analysis was performed to determine whether the different cytokine/chemokine transcript levels were dependent or independent variables with respect to predicting GC⁺ follicle presence in a sample. LT-β and BLC transcript levels were independent predictors of GC⁺ follicle presence in a sample (Table 1). Significance for SLC was lost after bootstrapping was performed to control for the sample size. None of the other parameters continued to be significant after correction for LT-β and BLC measurements.

These results demonstrate that elevated levels of cytokines and chemokines can be used to predict the presence of GC⁺ follicles in a sample. Specifically, these results indicate that elevated levels of LT-β and BLC transcripts are independent predictors of GC⁺ follicles in a sample. Therefore, statistical analysis of LT-β or BLC transcript levels, or the transcript levels of other related cytokines and chemokines, will serve to determine the severity of an RA condition.

TABLE 1

Multivariate logistic regression modeling for predicting the presence of GC⁺follicles

| Variable | Cutoff point* | Odds ratio (95% CI) | P |
| --- | --- | --- | --- |
| LT-β | 315 | 15.45 (2.72–87.59) | 0.002 |
| BLC | 1800 | 14.03 (2.22–88.58) | 0.005 |
| SLC | 550 | 14.17 (1.30–159.60) | 0.03‡ |
| LT-α | 110 | 3.56 (0.49–25.69) | 0.209 |
| MCP | 875 | 1.60 (0.26–9.96) | 0.617 |
| DC-CK 1 | 3840 | 999 (0.00–999.00) | 0.954 |

*Optimal cutoff points (number of transcripts) for cytokine concentrations were identified by recursive partitioning. Multivariate logistic regression models were developed using a stepwise approach.
‡Did not withstand bootstrap model validation.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining the severity of a rheumatoid arthritis condition in a mammal, said method comprising determining whether or not a sample comprising synovial tissue or synovial fluid from said mammal contains an elevated level of a CD21L polypeptide, wherein the presence of said elevated level indicates that said rheumatoid arthritis condition is severe.

2. A method of assisting a person in determining the severity of a rheumatoid arthritis condition in a mammal, wherein said method comprises:
   a) determining whether or not a sample comprising synovial tissue or synovial fluid from said mammal contains an elevated level of a CD21L polypeptide and
   b) communicating information about the presence or absence of said elevated level in said sample to said person, wherein the presence of said elevated level indicates that said rheumatoid arthritis condition is severe.

3. A method for determining the severity of a rheumatoid arthritis condition in a mammal, said method comprising determining whether or not a sample comprising synovial tissue or synovial fluid from said mammal contains an elevated level of an SLC polypeptide, wherein the presence of said elevated level indicates that said rheumatoid arthritis condition is severe.

4. A method of assisting a person in determining the severity of a rheumatoid arthritis condition in a mammal, wherein said method comprises:
   a) determining whether or not a sample comprising synovial tissue or synovial fluid from said mammal contains an elevated level of an SLC polypeptide, and
   b) communicating information about the presence or absence of said elevated level in said sample to said person, wherein the presence of said elevated level indicates that said rheumatoid arthritis condition is severe.

* * * * *

SEQUENCE LISTING

<160> NUMBER OF SEQ ID NOS: 23

<210> SEQ ID NO 1
<211> LENGTH: 21
<212> TYPE: DNA
<213> ORGANISM: Artificial Sequence
<220> FEATURE:
<223> OTHER INFORMATION: primer for PCR -continued

<400> SEQUENCE: 1
gtggatttac tttgaagggc a                                                    21

<210> SEQ ID NO 2
<211> LENGTH: 18
<212> TYPE: DNA
<213> ORGANISM: Artificial Sequence
<220> FEATURE:
<223> OTHER INFORMATION: primer for PCR

<400> SEQUENCE: 2
ggcatgtttc ttcacacc                                                        18

<210> SEQ ID NO 3
<211> LENGTH: 22
<212> TYPE: DNA
<213> ORGANISM: Artificial Sequence
<220> FEATURE:
<223> OTHER INFORMATION: primer for PCR

<400> SEQUENCE: 3
atcagggagg actggtaacg ga                                                   22

<210> SEQ ID NO 4
<211> LENGTH: 22
<212> TYPE: DNA
<213> ORGANISM: Artificial Sequence
<220> FEATURE:
<223> OTHER INFORMATION: primer for PCR

<400> SEQUENCE: 4
gaggtaatag aggccgtcct gc                                                   22

<210> SEQ ID NO 5
<211> LENGTH: 22
<212> TYPE: DNA
<213> ORGANISM: Artificial Sequence
<220> FEATURE:
<223> OTHER INFORMATION: primer for PCR

<400> SEQUENCE: 5
tctctgcttc tcatgctgct gg                                                   22

<210> SEQ ID NO 6
<211> LENGTH: 22
<212> TYPE: DNA
<213> ORGANISM: Artificial Sequence
<220> FEATURE:
<223> OTHER INFORMATION: primer for PCR

<400> SEQUENCE: 6
agcttgaggg tccacacaca ca                                                   22

<210> SEQ ID NO 7
<211> LENGTH: 21
<212> TYPE: DNA
<213> ORGANISM: Artificial Sequence
<220> FEATURE:
<223> OTHER INFORMATION: primer for PCR

<400> SEQUENCE: 7
atggccacgg ctgcttccag c                                                    21

<210> SEQ ID NO 8
<211> LENGTH: 21

```
<212> TYPE: DNA
<213> ORGANISM: Artificial Sequence
<220> FEATURE:
<223> OTHER INFORMATION: primer for PCR

<400> SEQUENCE: 8
catggtggtg ccgccagaca g                                              21

<210> SEQ ID NO 9
<211> LENGTH: 20
<212> TYPE: DNA
<213> ORGANISM: Artificial Sequence
<220> FEATURE:
<223> OTHER INFORMATION: primer for PCR

<400> SEQUENCE: 9
gctgctcacc tcattggaga                                                20

<210> SEQ ID NO 10
<211> LENGTH: 20
<212> TYPE: DNA
<213> ORGANISM: Artificial Sequence
<220> FEATURE:
<223> OTHER INFORMATION: primer for PCR

<400> SEQUENCE: 10
ggtggatagc tggtctccct                                                20

<210> SEQ ID NO 11
<211> LENGTH: 22
<212> TYPE: DNA
<213> ORGANISM: Artificial Sequence
<220> FEATURE:
<223> OTHER INFORMATION: primer for PCR

<400> SEQUENCE: 11
ccccaggacc caaggcagtg at                                             22

<210> SEQ ID NO 12
<211> LENGTH: 22
<212> TYPE: DNA
<213> ORGANISM: Artificial Sequence
<220> FEATURE:
<223> OTHER INFORMATION: primer for PCR

<400> SEQUENCE: 12
tgtgaccgct cagtcctctt gc                                             22

<210> SEQ ID NO 13
<211> LENGTH: 21
<212> TYPE: DNA
<213> ORGANISM: Artificial Sequence
<220> FEATURE:
<223> OTHER INFORMATION: primer for PCR

<400> SEQUENCE: 13
ggtgtcatcc tcctaaccaa g                                              21

<210> SEQ ID NO 14
<211> LENGTH: 20
<212> TYPE: DNA
<213> ORGANISM: Artificial Sequence
<220> FEATURE:
<223> OTHER INFORMATION: primer for PCR

<400> SEQUENCE: 14
```
ggaaagggga aaggatgata                                          20

<210> SEQ ID NO 15
<211> LENGTH: 20
<212> TYPE: DNA
<213> ORGANISM: Artificial Sequence
<220> FEATURE:
<223> OTHER INFORMATION: primer for PCR

<400> SEQUENCE: 15
gctcagccag atgcaatcaa                                          20

<210> SEQ ID NO 16
<211> LENGTH: 20
<212> TYPE: DNA
<213> ORGANISM: Artificial Sequence
<220> FEATURE:
<223> OTHER INFORMATION: primer for PCR

<400> SEQUENCE: 16
gcaatttccc caagtctctg                                          20

<210> SEQ ID NO 17
<211> LENGTH: 20
<212> TYPE: DNA
<213> ORGANISM: Artificial Sequence
<220> FEATURE:
<223> OTHER INFORMATION: probe for cloning

<400> SEQUENCE: 17
ttccttcctg ggcatggagt                                          20

<210> SEQ ID NO 18
<211> LENGTH: 23
<212> TYPE: DNA
<213> ORGANISM: Artificial Sequence
<220> FEATURE:
<223> OTHER INFORMATION: probe for cloning

<400> SEQUENCE: 18
ccagtggcat ctacttcgtc tac                                      23

<210> SEQ ID NO 19
<211> LENGTH: 23
<212> TYPE: DNA
<213> ORGANISM: Artificial Sequence
<220> FEATURE:
<223> OTHER INFORMATION: probe for cloning

<400> SEQUENCE: 19
gaggagccag aaacagatct cag                                      23

<210> SEQ ID NO 20
<211> LENGTH: 22
<212> TYPE: DNA
<213> ORGANISM: Artificial Sequence
<220> FEATURE:
<223> OTHER INFORMATION: probe for cloning

<400> SEQUENCE: 20
tccctagacg cttcattgat cg                                       22

<210> SEQ ID NO 21
<211> LENGTH: 22
<212> TYPE: DNA
<213> ORGANISM: Artificial Sequence -continued

```
<220> FEATURE:
<223> OTHER INFORMATION: probe for cloning

<400> SEQUENCE: 21
ctccatccca gctatcctgt tc                                               22

<210> SEQ ID NO 22
<211> LENGTH: 24
<212> TYPE: DNA
<213> ORGANISM: Artificial Sequence
<220> FEATURE:
<223> OTHER INFORMATION: probe for cloning

<400> SEQUENCE: 22
cttttaagag tcccatctgc tatg                                             24

<210> SEQ ID NO 23
<211> LENGTH: 23
<212> TYPE: DNA
<213> ORGANISM: Artificial Sequence
<220> FEATURE:
<223> OTHER INFORMATION: probe for cloning

<400> SEQUENCE: 23
gaagacttga acactcactc cac                                              23
```